United States Patent [19]
Barbut et al.

[11] Patent Number: 6,136,025
[45] Date of Patent: Oct. 24, 2000

[54] ENDOSCOPIC ARTERIAL PUMPS FOR TREATMENT OF CARDIAC INSUFFICIENCY AND VENOUS PUMPS FOR RIGHT-SIDED CARDIAC SUPPORT

[76] Inventors: Denise R. Barbut, 70 E. 70th St., New York, N.Y. 10021; Russell H. Patterson, 146 57th St., New York, N.Y. 10019; Mark-Hein Heinemann, 70 E. 70th St., New York, N.Y. 10021

[ * ] Notice: This patent issued on a continued prosecution application filed under 37 CFR 1.53(d), and is subject to the twenty year patent term provisions of 35 U.S.C. 154(a)(2).

[21] Appl. No.: 09/362,992

[22] Filed: Jul. 27, 1999

[51] Int. Cl.$^7$ ........................................ A61M 1/10
[52] U.S. Cl. .............................. 623/3.1; 604/96; 604/530; 606/194; 606/198; 623/3.15
[58] Field of Search .......................... 604/96, 264, 523, 604/530, 532; 606/194, 198, 191; 623/3.1, 3.13, 3.15, 322, 3.24, 3.25, 3.26

[56] References Cited

U.S. PATENT DOCUMENTS

| | | | |
|---|---|---|---|
| 4,944,722 | 7/1990 | Carriker et al. | 600/16 |
| 5,147,388 | 9/1992 | Yamazaki | 623/2 |
| 5,234,257 | 8/1993 | Andersen | 606/198 |
| 5,261,878 | 11/1993 | Galindo | 604/96 |
| 5,735,897 | 4/1998 | Buirge | 623/12 |
| 5,746,709 | 5/1998 | Rom et al. | 604/8 |
| 5,810,708 | 9/1998 | Woodwar et al. | 600/16 |
| 5,810,836 | 9/1998 | Hussein et al. | 606/108 |
| 5,827,171 | 10/1998 | Dobak, III et al. | 600/16 |
| 5,882,329 | 3/1999 | Patterson et al. | 604/49 |

FOREIGN PATENT DOCUMENTS

WO 95/10989   4/1995   WIPO .

*Primary Examiner*—Corrine McDermott
*Assistant Examiner*—LoAn H. Thanh
*Attorney, Agent, or Firm*—Lyon & Lyon LLP

[57] ABSTRACT

Methods for using blood pumps to treat heart failure are disclosed. The pump is mounted on an interior of a stent, does not occupy the entire lumen, and the stent is releasably mounted on a distal end of a catheter. The distal end of the catheter is inserted into a peripheral artery and advanced to position the stent at a region of interest within the descending aorta, the ascending aorta, or the left ventricle. The stent and the pump are released from the catheter, and the pump is activated to increase blood flow downstream of the pump. The pump can also be positioned in the vena cava or used to treat right-sided heart failure following the insertion of an LVAD, or to improve venous return in patients with varicose veins. Non-stent pumps are described for insertion between the pulmonary vein and aorta, and between the vena cava and pulmonary artery designed for use during cardiac surgery.

20 Claims, 10 Drawing Sheets

ENDOSCOPIC ARTERIAL PUMPS FOR TREATMENT OF CARDIAC INSUFFICIENCY AND VENOUS PUMPS FOR RIGHT-SIDED CARDIAC SUPPORT

FIELD OF THE INVENTION

The present invention relates generally to methods useful for treating patients with heart failure and cardiogenic shock. More specifically, the invention provides means for implanting a blood pump endoscopically in arteries, such as the descending aorta, the ascending aorta, the left ventricle, or the pulmonary vein to assist the failing left ventricle and improve perfusion to vital organs. The pump may provide continuous or intermittent flow. The device can also be implanted endoscopically in veins, such as the inferior vena cava, the right atrium or pulmonary artery for treatment of right heart failure or venous insufficiency.

BACKGROUND OF THE INVENTION

Heart failure has a prevalence in the United States of more than 2 million patients with at least 400,000 new cases diagnosed each year. Mean life expectancy following a diagnosis of cardiac failure is less than 2 years. Heart failure is responsible for at least 200,000 deaths each year, with annual costs estimated to exceed 10 billion dollars.

Most cases of heart failure are caused by left ventricular dysfunction, due to myocardial hypocontractility from coronary ischemia. Other causes of left ventricular failure include non-ischemic conditions such as idiopathic cardiomyopathy or dilated cardiomyopathy due to toxins (such as alcohol and cocaine), infections (such as coxsackievirus, trichinosis, and lyme disease), or infiltration (such as in hemochromotosis and sarcoidosis).

Cardiogenic shock, the end-stage of cardiac failure, occurs in 150,000 patients per year in the United States. Although advances in medical and surgical therapy, e.g., pharmacotherapy and emergency coronary artery bypass grafting surgery, have benefited a few of these patients, the majority are refractory to standard medical and surgical treatment. For these patients, heart transplantation is the only proven treatment. However, fewer than 3,000 donor hearts become available each year. Even in patients accepted for transplantation, a significant waiting list mortality has been observed.

A variety of ventricular assist devices (VADs) have been invented since the development of the first successful case of mechanical assistance over 30 years ago to support patients suffering from acute but reversible ventricular failure and to sustain patients who are candidates for transplantation. The first generation of VADs, developed by the early 1980s, consisted of external pumps connected to a patient's heart by surgically implanted cannulae. The Abiomed BVS 5000 system was widely used for short-term cardiac support as a bridge to transplant in 1992. Other VADs utilizing external pneumatic pumps for short-term support include the Thoratec Ventricular Assist Device and the CardioWest VAD. Disadvantages associated with these external VADs are that (1) multiple large surgical incisions, including median sternotomy and perforation of the ventricle, to connect the support system to the heart are required, (2) the surgical sites pose continuing risk of infection and other complications, such as hemorrhage, (3) the large console needed to house power and control systems severely limits the patient's mobility, thereby requiring hospitalization for the patients.

To overcome the disadvantages associated with the external VADs, pumps small enough to be fully implanted within a patient's body were developed. Two other implantable VADs, the TCI HeartMate and the Novacor Ventricular Assist System, have been developed for long-term use in heart failure patient as an alternative to cardiac transplantation. These devices consist of implantable pumps connected to the left ventricle and the aorta through extracardiac blood conduits. These devices, however, are associated with high complication rates, including (1) substantial morbidity due to the median sternotomy (Nocacor) with cardiac mobilization, often in patients who have had previous cardiac surgery, (2) morbidity due to extensive dissection of the abdominal wall to create a pocket for the pump, (3) bleeding requiring re-operation (30%), (4) bleeding from anticoagulation use, (5) infection (50%) (both nosocomial and device related), (6) thromboembolism, especially to the brain (cerebral emboli were detected using transcranial doppler in two thirds of the patients with ventricular assist devices), and (7) significant bleeding associated with the extensive surgery often results in right heart failure (20%).

The "Acorn device," a metallic envelope which surrounds the ventricles to prevent progressive cardiac dilatation and facilitate ventricular contraction during systole, has been developed to bypass the complications associated with the implantable VADs. Unfortunately, the Acorn device also requires surgical implantation, and its efficacy has not yet been tested in humans.

To reduce morbidity associated with extensive surgical procedures, such as median sternotomy, an endoscopically insertable intraventricular pump (hemopump) is being developed. This device is inserted endoscopically, through the aortic valve and into the left ventricle. The hemopump is capable of delivering blood at 1.5 to 2 liters per minute, with demonstrated mild improvements in hemodynamic parameters. However, peri-procedural morbidity associated with using this device is high, including stroke. Systemic anticoagulation is usually necessary for its insertion and is associated with increased risk of hemorrhage. Failure of device insertion occurs in 25% of patients, partly due to iliofemoral atheromatosis and inability to cross the aortic valve. The hemopump is contraindicated in patients with ascending aortic aneurysms, aortic stenosis, aortic regurgitation, and/or artificial aortic valves. Apart from having high complication rates, an additional problem associated with using the existing VADs is that patients can not be weaned from the VADs without another surgical procedure to remove the implanted devices.

What is needed are simpler and safer methods for treating patients with heart failure refractory to medical therapy without the need for surgical procedures, and with fewer associated complications. Existing devices are inadequate for this purpose.

SUMMARY OF THE INVENTION

Various blood pumps have been developed for insertion in arteries and are well known in the art. Suitable devices for use in the invention herein are disclosed in Rise, U.S. Pat. No. 5,643,207; Elsberry et al., U.S. Pat. Nos. 5,711,316, 5,735,814, 5,814,014, and 5,832,932; Rom, U.S. Pat. No. 5,746,709; Patton et al., U.S. Pat. No. 5,759,017; Robinson, U.S. Pat. No. 5,840,069; Torgerson et al., U.S. Pat. No. 5,820,589; Allen et al., *Artificial Organs* 21(8):922–928 (1997); and Sieb et al., *Artificial Organs* 19(7):644–652 (1995), all of which are incorporated herein by reference in their entirety. The present invention provides methods for endoscopic placement of blood pump(s) in a patient's blood vessel(s) for treatment of heart failure and/or severe venous insufficiency. More specifically, the invention utilizes a catheter having an expandable stent releasably mounted on a distal end of the catheter for deployment of the blood pump. The blood pump can be endoscopically deployed within a region of interest in an artery or vein, and can be removed without any surgical procedures when its assistance is no longer required.

In the first embodiment of the device, we assist the heart by placing a pump in the descending aorta and removing it when no longer necessary. This would be designed both for short term and long term use. The blood pump is mounted in an interior of the stent, and would occupy only a fraction of the stent lumen when expanded. The diameter of the pump may be no more than the diameter of the femoral artery, 0.5–1 cm, or 14–16 French, while the diameter of the deployed stent to which it was attached would be slightly more than the diameter of the aorta. This would provide a means for attaching the pump to the aortic wall, while allowing it to be introduced endovascularly. The length of the pump would be 5–10 cm, as would the stent. The stent with the pump is placed, in certain embodiments, in the descending aorta, just beyond the takeoff of the left subclavian artery. Thus, any thromboembolic complication would be distal, and would not involve the brain.

In a first method for treatment of heart failure, the blood pump is mounted in an interior of the stent. The stent (or the pump, or both) may be made of a memory retaining biocompatible material, such as nitinol, which allows the stent to be compressed before deployment to facilitate insertion into a vessel, and thereafter self-expand intravascularly. Alternatively, the catheter includes an angioplasty balloon, which upon inflation expands the stent intravascularly. The distal end of the stent-deployment catheter is inserted into a peripheral artery, e.g., the subclavian artery or the femoral artery, and advanced to position the stent within the descending aorta, just beyond the takeoff of the left subclavian artery. Thus, any thromboembolic complication would be distal to the takeoff of the left subclavian artery and would not involve the brain. The stent is then expanded. The stent and the pump are released from the catheter, and the pump is activated to increase arterial blood flow downstream of the pump. Alternatively, the stent is expanded before being released. A manometer may be included in a distal end and/or a proximal end of the pump for measuring blood pressure upstream and/or downstream the pump. Radiopaque material may be mounted on the pump or the stent, thereby allowing fluoroscopic verification of the positioning.

The pump/stent may accommodate other endovascular devices, such as an angioplasty catheter or atherectomy catheter, during high risk angioplasty procedures. The endovascular catheter can be inserted through the space between the pump and the stent to reach the stenotic lesion in the coronary arteries and/or the aorta. Since in the first embodiment, the pump/stent is deployed in the aorta and insertion through the aortic valve is not required, the rate of failure of insertion is considerably lower than for the hemopump, and the pump/stent can be used in patients with contraindication to using the hemopump, such as in patients with aortic valve regurgitation, aortic valve replacement, or aortic stenosis. Cardiac arrhythmia, a common complication associated with the hemopump, is avoided since the pump/stent does not engage any myocardial or endocardial tissues.

The pump is capable of delivering blood flow at approximately 1.5 liters per minute, more preferably at 2 liters per minute, more preferably at 2.5 liters per minute, more preferably at 3 liters per minute, more preferably at 3.5 liters per minute, more preferably at 4 liters per minute, more preferably at 4.5 liters per minute, more preferably at 5 liters per minute. Pumps capable of delivering up to 5 liters per minutes have been constructed and are well known in the art. The smallest of these pumps weighs only 53 grams, and has a diameter no more than the diameter of the femoral artery, i.e., 0.5 to 1.0 centimeters, or 14 to 16 French. Hemodynamic improvement has been shown with flow augmentation at 1.5 to 2 liters per minute. The pump may be an electrically activated, continuous-flow, high speed helical pump. Operation of the pump is continuous.

In certain embodiments of the pump, a wire, having proximal and distal ends, may be connected to the pump at the distal end and a battery at the proximal end. The battery is placed subcutaneously and powered telemetrically, thereby reducing the risk of infection associated with placement of the battery outside a patient's body. The design and construction of telemetrically-powered batteries is explained in numerous references well-known to those having ordinary skill in the art, all of which are incorporated herein by reference, and will not be further discussed herein. Alternatively, the battery is placed at the core of the pump. In certain embodiments, two or more batteries or pumps are placed in sequence to allow for separate recharging. Anticoagulants, such as heparin and heparinoids, may be applied to the stent and the pump to reduce the chances of blood clotting. Anticoagulants other than heparinoids also may be used, e.g., monoclonal antibodies such as ReoPro (Centocor). The anticoagulant may be painted or sprayed onto the pump and/or the stent. A chemical dip comprising the anticoagulant also may be used. Other methods known in the art for applying chemicals to a stent and pump may be used. Systemic anticoagulation may or may not be required.

In another method, the distal end of the catheter is inserted through a peripheral artery and advanced to position the stent at a region of interest within the ascending aorta upstream of the brachiocephalic artery. Blood delivered by the pump maintains perfusion to the peripheral organs including the brain. This method is particularly useful in treating patients with global cerebral ischemia to augment blood flow to the cerebral vasculature. The dosage of systemically administered afterload reducing agents can therefore be reduced to avoid unwanted side effects.

The pump and stent described herein can also be modified, such that the stent is mounted around a proximal end of the pump. When the stent is deployed in the ascending aorta, the distal end of the pump protrudes beyond the stent and extends through the aortic valve into the left ventricle. The pump width will be approximately 16 French. In this method, the aortic valve and lumen would not be entirely occupied by the pump, since the aortic valve width is generally between 2 and 3 centimeters. A major advantage of this embodiment is that device failure would not lead to outlet obstruction. This embodiment could also be used during cardiac surgery. An external antegrade or retrograde valve could be positioned outside the protruding end of the pump to control flow in both directions.

In certain embodiments, one or more balloon occluders, rather than a stent, are mounted on the proximal and/or distal ends of the pump. When the pump is inserted with its proximal end positioned in the ascending aorta, the distal end of the pump can extend into the pulmonary vein. This embodiment enables open left heart surgery to be performed in both beating heart or stopped heart procedures, since the occluding balloons prevent blood from leaking and emptying into the left ventricular cavity. The balloon occluder mounted on the aortic end of the pump provides circulatory isolation of coronary blood flow from the peripheral circulation, thereby replacing aortic cross-clamp application. This embodiment is therefore designed more for use during cardiac surgery than for long-term use.

The pump and stent described herein can also be deployed in veins to improve venous return to the heart. The pump attached to the stent can be deployed in the inferior vena cava for treatment of right ventricular failure, a common complication following deployment of left ventricular assist devices. The pump and stent can also be used to treat varicose veins and severe venous insufficiency of the lower extremities. If the symptoms are unilateral, the pump and stent can be deployed in the peripheral veins, such as the iliac vein or the femoral vein. Another embodiment without the stent could be deployed between the vena cava and the pulmonary artery, or the right ventricle and the pulmonary artery, with occluding balloons in the right atrium and pulmonary artery preventing leakage of blood. Right- or left-sided intra-cardiac pumps would be indicated during cardiac surgical procedures, rather than for long-term use.

In cases of pump malfunctioning or improvement in the patient's hemodynamic status, the pump/stent can be removed endovascularly, thereby avoiding a surgical procedure. It is known that in approximately 30% of patients with heart failure, the heart is able to recover sufficiently to function without assistance after a period of rest afforded by the pump. Alternatively, the pump may be inactivated but left in situ for use in a next episode of heart failure without obstructing the circulation. The existing VADs, including the hemopump, have to be surgically removed (the hemopump especially since it can obstruct the aortic outflow tract). Therefore, salvage of the pump in case of malfunctioning or improvement in the patient's condition would then clearly be endovascular, rather than requiring a second surgical procedure. Such retrieval may be crucial in the design of assist devices.

It will be understood that there are several advantages in using the methods described herein for endoscopically deploying a blood pump/stent. For example, by using the pump (1) major surgical procedures can be avoided, (2) numerous complications associated with the existing VADs, such as cardiac arrhythmia, bleeding, thromboembolism to the brain, and infection, can be minimized or avoided, (3) the patient can be easily weaned from the pump when ventricular support is not required, (4) the pump/stent can be easily removed or replaced endoscopically like any other stent without surgical procedures, (5) patients with contraindications to the existing VADs can be treated without complication (the only contraindication to using the disclosed methods is aortic aneurysm), (6) the pump is easily placed under angiography, (7) the pump can accommodate an angioplasty, atherectomy, or other therapeutic catheter during high-risk endovascular procedures, (8) the pump can be used during stopped heart cardiac surgery, and (9) the pump can be used to treat venous insufficiency in addition to treating heart failure.

DETAILED DESCRIPTION

Although endoscopic deployment of the pump utilizing a stent is most useful in treating patients with heart failure, the methods disclosed herein can be used to treat a variety of conditions involving arterial and/or venous insufficiency. The pump can be deployed in a vessel which supplies a vital organ, e.g., in the renal artery to increase flow to the kidneys. The pump(s) can be deployed in any vessel where augmentation of blood flow is needed.

Figure 1A:
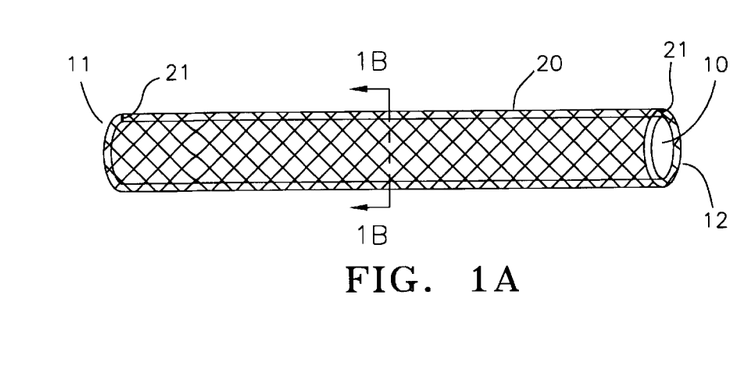
FIG. 1A depicts a lateral view of a blood pump disposed within a stent before deployment.
Figure 1B:
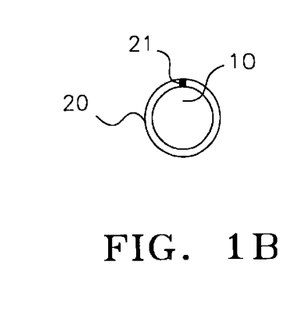
FIG. 1B depicts a cross-sectional view through line B—B of the pump/stent assembly of FIG. 1A.
Figure 1C:
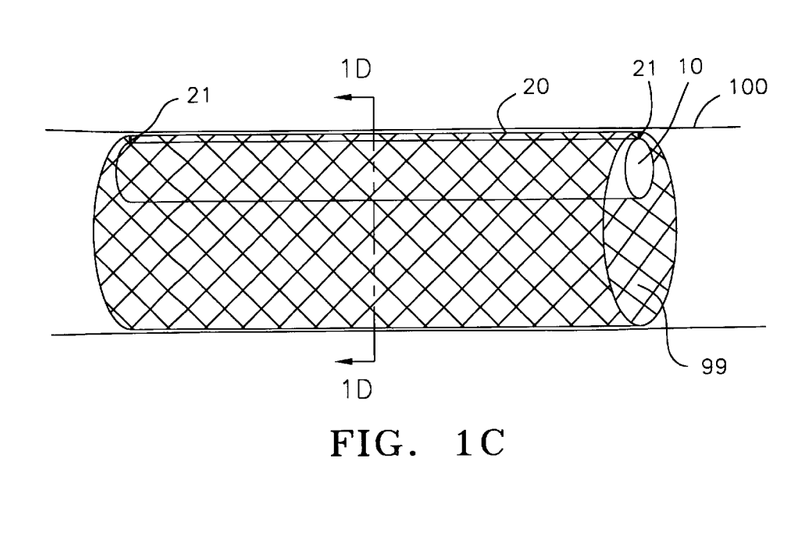
FIG. 1C depicts the pump/stent assembly of FIG. 1A deployed in a vessel.
Figure 1D:
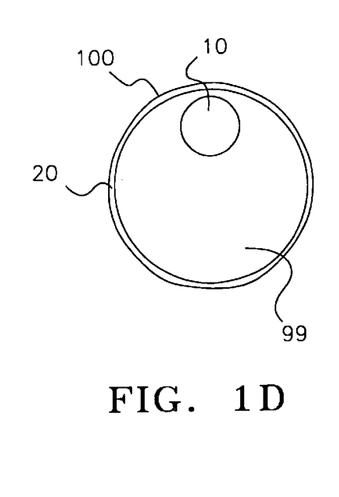
FIG. 1D depicts a cross-sectional view through line D—D of the pump/stent assembly of FIG. 1C.

In FIG. 1A, pump 10 is disposed within stent 20. Proximal end 11 and distal end 12 of the pump are attached to stent 20 by direct bonding or through anchoring elements 21. FIG. 1B provides a cross sectional view of the pump/stent assembly. The stent is made of a memory retaining biocompatible material, e.g., nitinol, and can be placed in a collapsed condition before deployment to facilitate insertion into a vessel. The pump/stent assembly is releasably mounted on a distal end of a catheter. In treating patients with congestive heart failure, the distal end of the catheter is inserted into a peripheral artery. The catheter is advanced to position the stent at a region of interest in the descending aorta. The stent is expanded, and the pump/stent assembly now positioned in aorta 100 is released from the catheter as depicted in FIG. 1C. Pump 10 can then be activated to augment arterial blood flow downstream of the pump. Pump 10 occupies a fraction of the stent lumen as depicted in FIG. 1D, allowing insertion of an endovascular catheter, e.g., an angioplasty or atherectomy catheter through gap 99. The catheter can be advanced distally to treat a stenotic vascular occlusion. The pump can be easily inserted and removed in high-risk patients (e.g., patients with poor ventricular function) undergoing endovascular procedures.

Figures 2A, 2B:
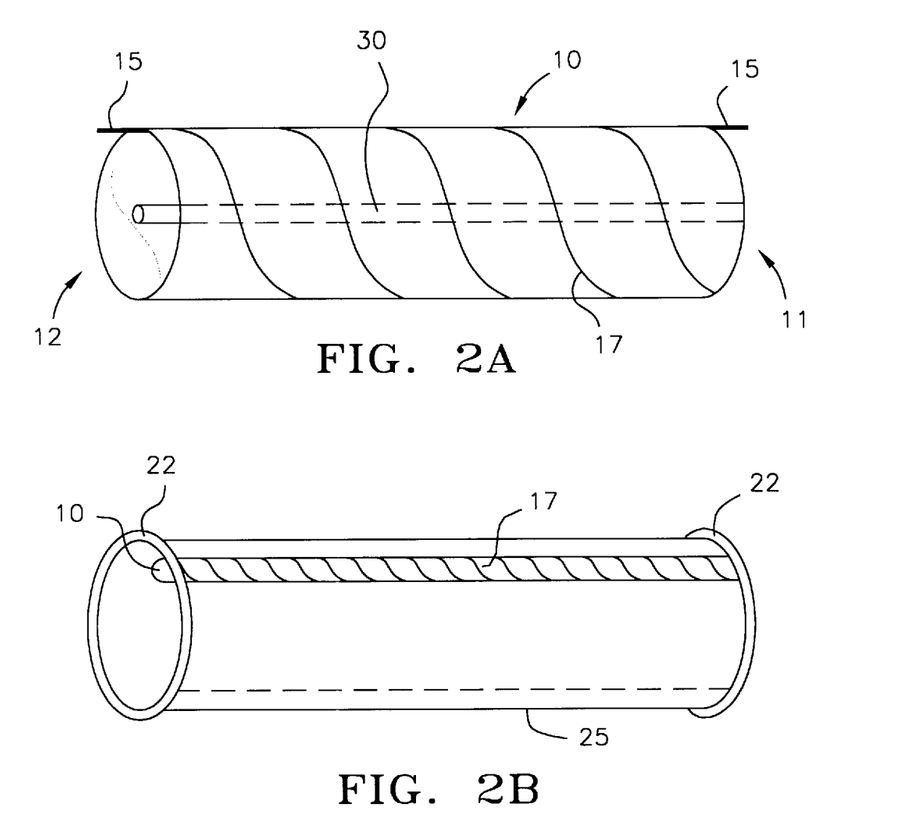
FIG. 2A depicts an embodiment of the pump including proximal and distal manometers.
FIG. 2B depicts another embodiment of the pump having an inflation seal at its proximal and distal ends.
Figure 2C:
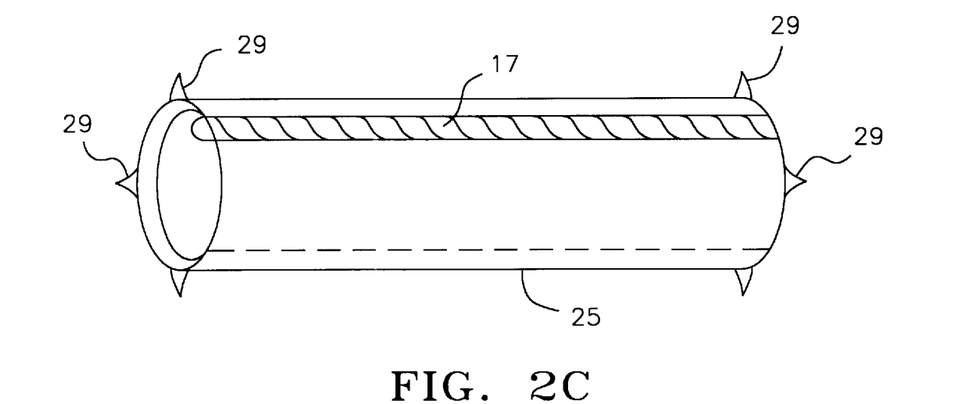
FIG. 2C depicts another embodiment of the pump having vessel-engaging hooks at its proximal and distal ends.

FIGS. 2A, 2B, and 2C depict different embodiments of the blood pump. In FIG. 2A, the outer surface of pump 10 has 2, 3, 4, 5, 6, 7, or other suitable number of helical grooves 17, such that the pump is like a cork-screw. Upon activation, the grooves spin, and blood is delivered from upstream the pump and passed along grooves 17, and exits downstream the pump. Battery 30 is disposed in the center of the pump or alternatively outside the blood vessel. Manometers 15 are mounted on distal end 11 and proximal end 12 of the pump for measuring, respectively, blood pressure downstream and upstream of the pump.

In FIG. 2B, pump 10 is disposed within tubular member 25. Inflation seals 22 are mounted at proximal and distal ends of the tubular member/stent. Each inflation seal has an inflation chamber which communicates with an inflation lumen in the catheter, and can be inflated by injecting fluid or gas into the inflation chamber. When inflated, the inflation seals engage the inner vessel wall, thereby stabilizing tubular member 25 and pump 10 against the vessel wall to prevent displacement from the blood flow. Alternatively, tubular member 25 and pump 10 can be anchored to the vessel wall by a plurality of hooks 29 mounted on the proximal and distal ends of the tubular member as depicted in FIG. 2C.

Figure 3:
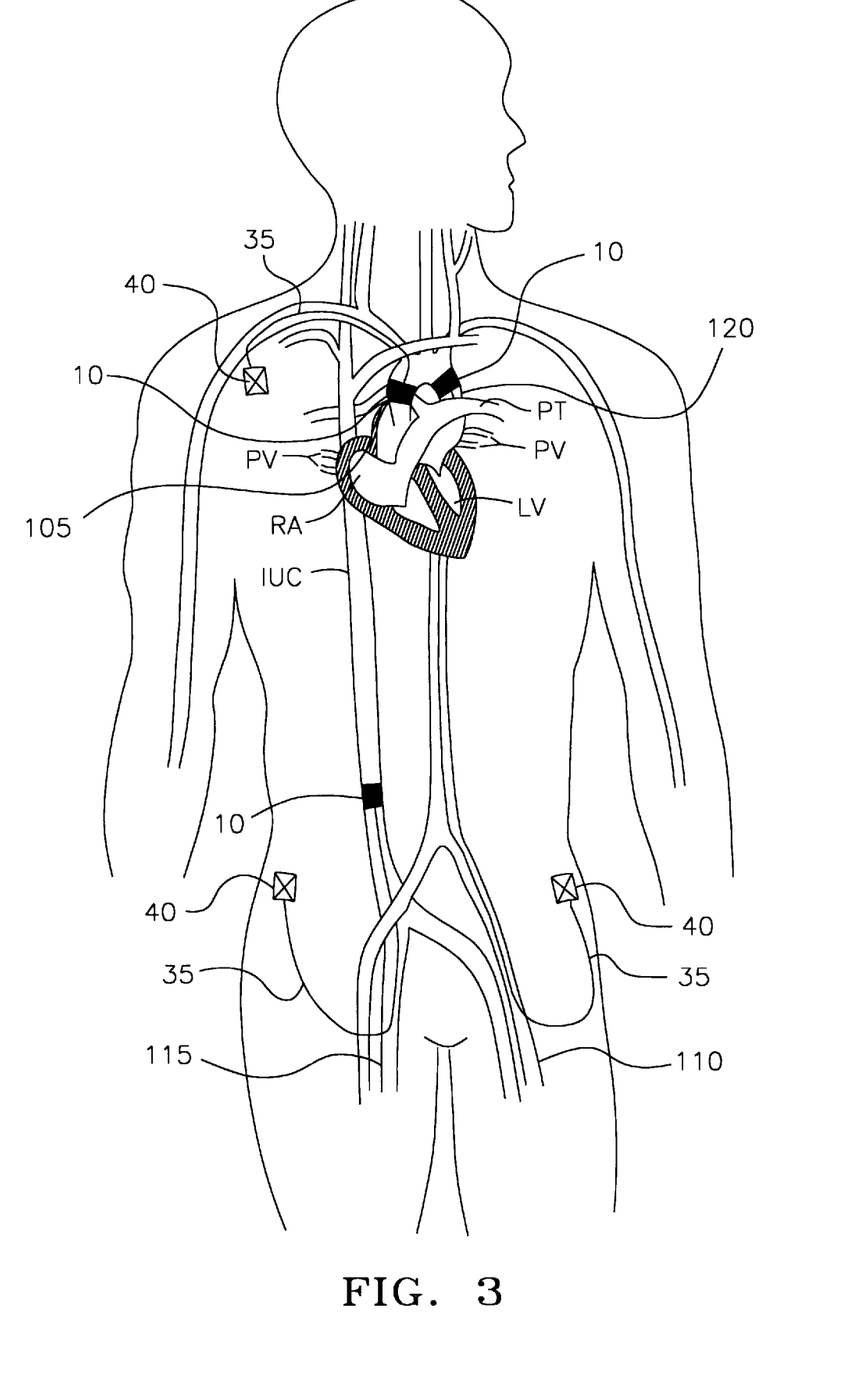
FIG. 3 depicts the pumps being connected to subcutaneously placed batteries.

The pump may be connected to a battery placed subcutaneously through wire 35 as depicted in FIG. 3. Pump 10 is shown placed in ascending aorta 105 and connected through wire 35 to battery 40, which is placed subcutaneously in the right chest wall. This is similar to placement of a cardiac pacemaker or defibrillator. The battery can be powered telemetrically. The risk of infection associated with subcutaneous placement of the battery is significantly reduced compared to the existing VADs having external batteries. When pump 10 is inserted through left femoral artery 110 into descending aorta 120 distal to the takeoff of the left subclavian artery, the pump is connected through wire 35 to battery 40 placed subcutaneously in the left lower quadrant of the abdominal wall. When pump 10 is inserted through right femoral vein 115 to deploy in the inferior vena cava, the pump is connected through wire 35 to battery 40 placed subcutaneously in the right lower quadrant of the abdominal wall. In this way, the battery can be easily replaced or removed when malfunctioning occurs.

Figure 4:
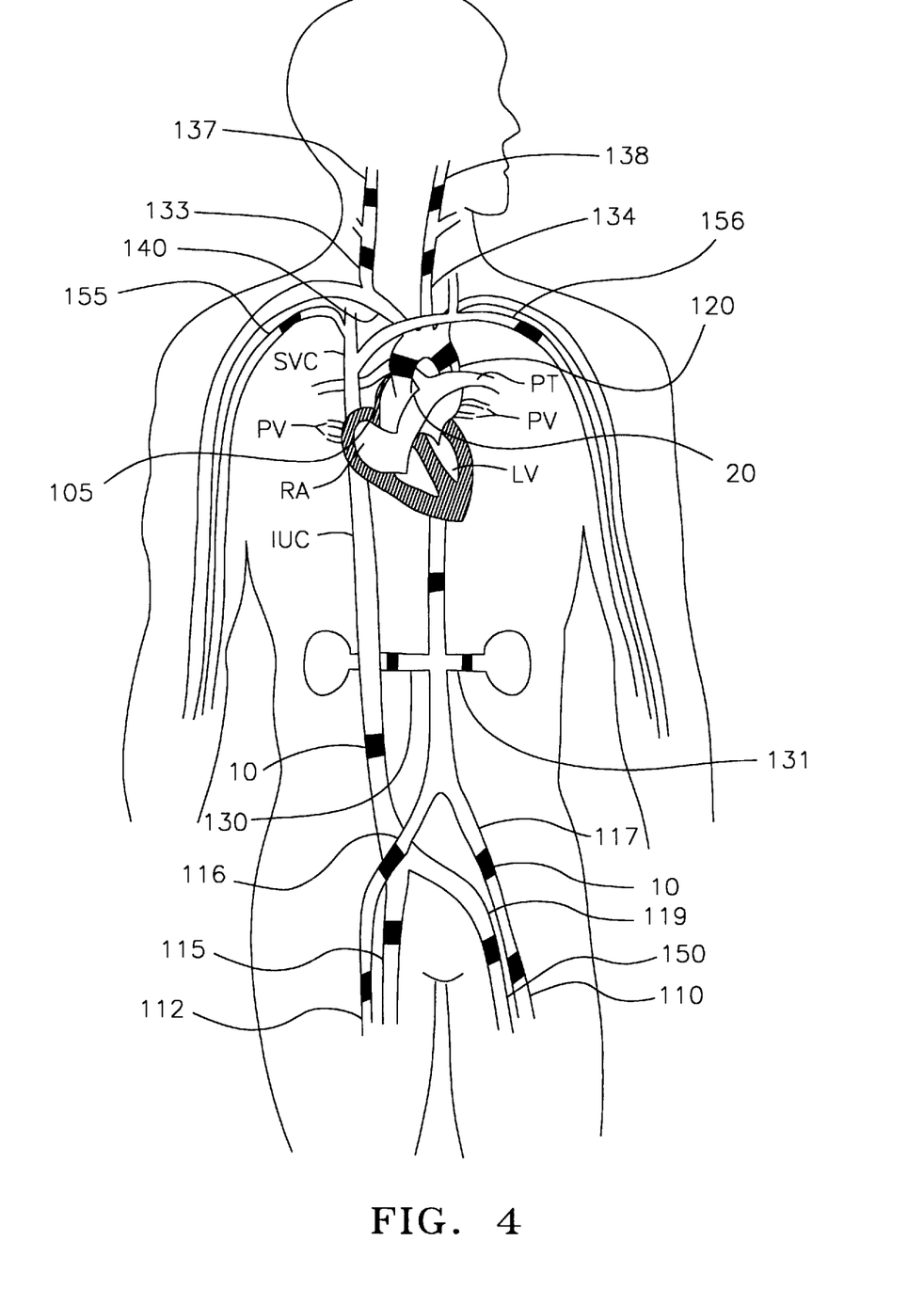
FIG. 4 depicts various locations in a patient's arteries and veins for deployment of the pump.

The pumps can be inserted in a patient's arteries and/or veins to increase blood flow to the peripheral organs and/or increase venous return to the heart. In FIG. 4, pump 10 can be deployed endoscopically in ascending aorta 105, descending aorta 120, right femoral artery 112, left femoral artery 110, right iliac artery 116, left iliac artery 117, right renal artery 130, left renal artery 131, right common carotid artery 133, left common carotid artery 134, right internal carotid artery 137, left internal carotid artery 138, right brachiocephalic artery 140, and pulmonary vein to the aorta. Pump 10 can also be deployed in right femoral vein 115, left femoral vein 150, the inferior vena cava, right subclavian vein 155 for treatment of varicose veins or severe venous insufficiency, or in the left subclavian 156, right atrium, or pulmonary artery for treatment of venous insufficiency.

Figure 5:
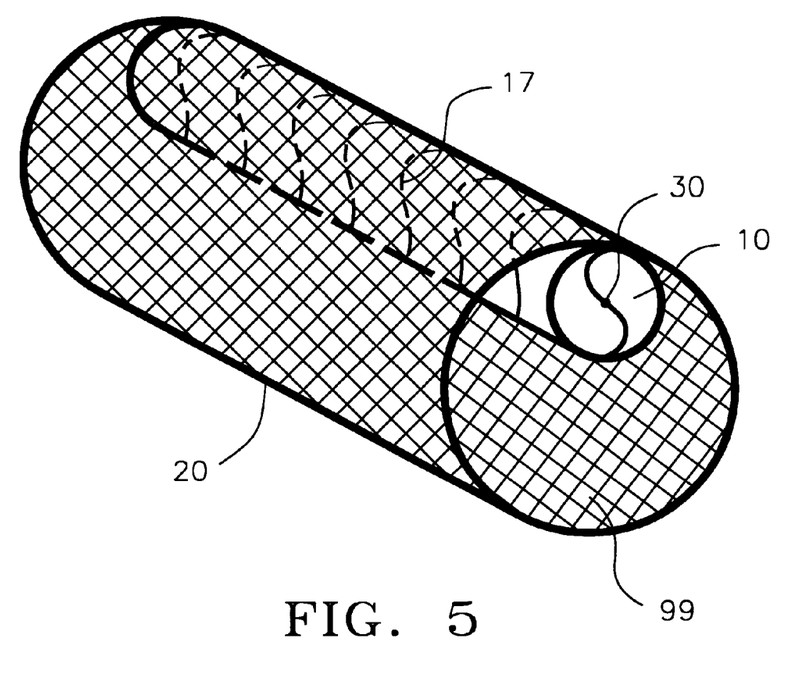
FIG. 5 depicts an oblique view of a pump/stent assembly utilizing a helical pump as shown in FIG. 2A.

FIG. 5 depicts another embodiment of the pump/stent assembly utilizing the helical pump of FIG. 2A. When deployed in a vessel, pump 10 occupies only a fraction of the stent lumen. Gap 99, the space between the pump and the stent, allows insertion of various endovascular devices, e.g., an angioplasty catheter, an atherectomy catheter, an endovascular imaging device, and/or an ablation catheter. Upon activation, helical grooves 17 of the pump spin, and blood is delivered from upstream the pump and passed along grooves 17, and exits downstream the pump. Battery 30 is shown disposed in the center of the pump.

Figure 6A:
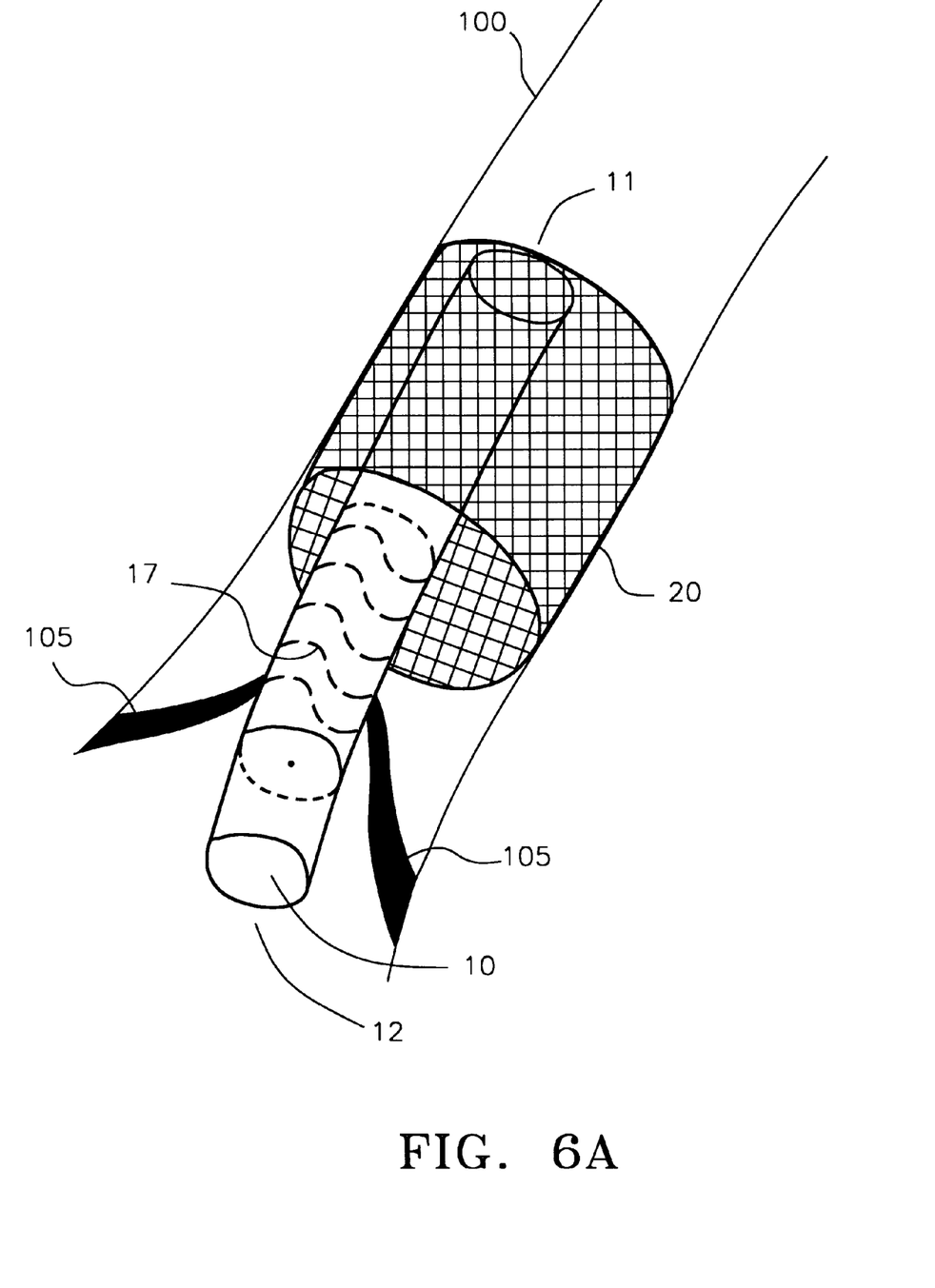
FIG. 6A depicts another embodiment of the pump/stent assembly positioned in the ascending aorta, having the pump extending across the aortic valves.
Figure 6B:
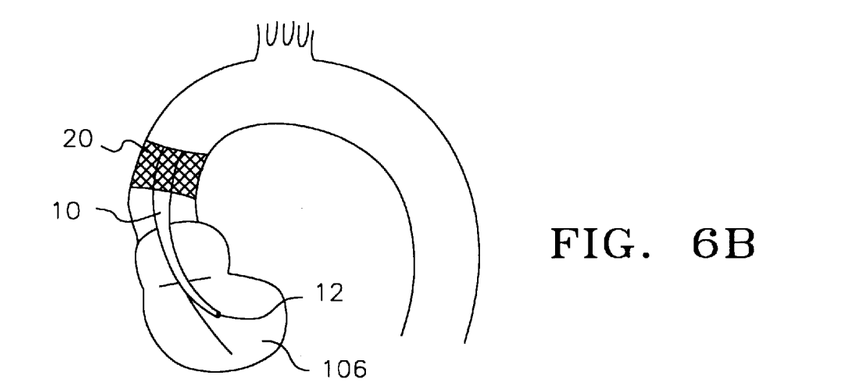
FIG. 6B depicts another embodiment of the pump/stent assembly positioned in the ascending aorta, having the pump extending into the left ventricle.

In certain embodiments of the pump/stent assembly, stent 20 is mounted on proximal end 11 of pump 10 as depicted in FIGS. 6A and 6B. In FIG. 6A, stent 20 is deployed in ascending aorta 100, with distal end 12 of pump 10 extending across aortic valves 105. In FIG. 6B, distal end 12 of pump 10 extends into left ventricle 106. Upon activation of the pump, blood is delivered from upstream the pump in the left ventricle and passed along helical grooves 17, and exits downstream the pump to the ascending aorta. In these embodiments, pump 10 does not occupy the entire aortic valve lumen, and therefore will not cause aortic outflow tract obstruction during pump failure. These embodiments are suitable for use in cardiac surgeries, such as coronary artery bypass, ventricular aneurysmectomy, or ventricular septal defect repair.

Figure 7:
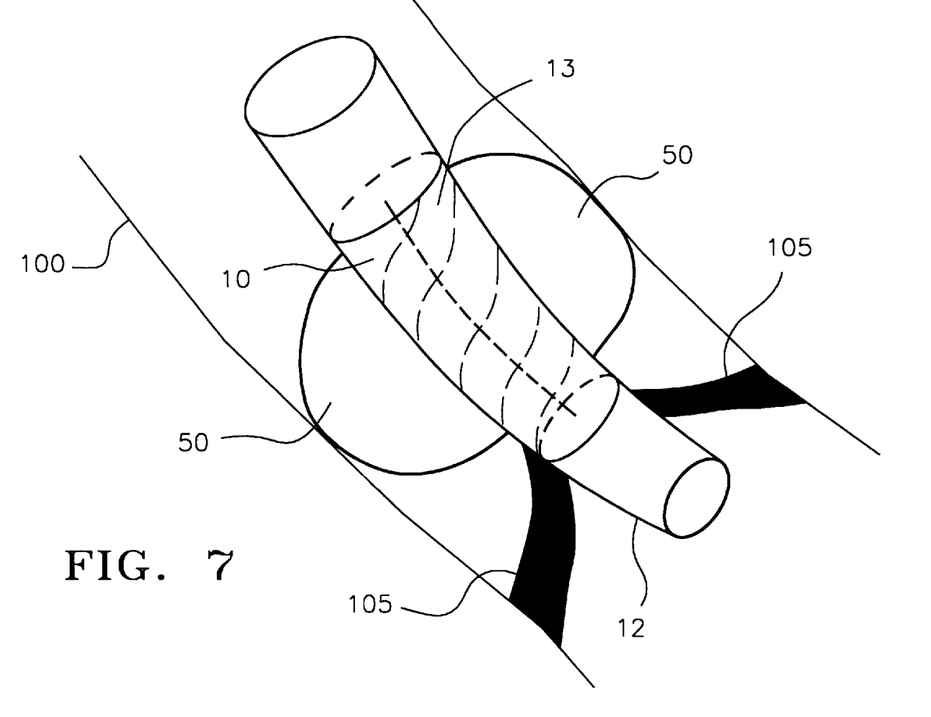
FIG. 7 depicts a pump having a balloon occluder which positions the pump in the ascending aorta.

FIG. 7 depicts another embodiment of the pump having balloon occluder 50 mounted in proximal region 13 of the pump. The pump can be mounted on a distal end of a catheter and inserted through a peripheral artery to position in ascending aorta 100. Instead of using a stent, pump 10 is secured in the ascending aorta above aortic valves 105 by inflating balloon occluder 50. When used in cardiac surgeries, the balloon occluder can replace an aortic crossclamp to provide circulatory isolation of coronary and peripheral blood flow for cardiopulmonary bypass. In another embodiment, an external valve with antegrade or retrograde flow would replace the balloon occluder and achieve the same purpose. The pump can also be inserted in the inferior or superior vena cava with distal end 12 extending into the right atrium, thereby facilitating venous return to the heart.

Figure 8:
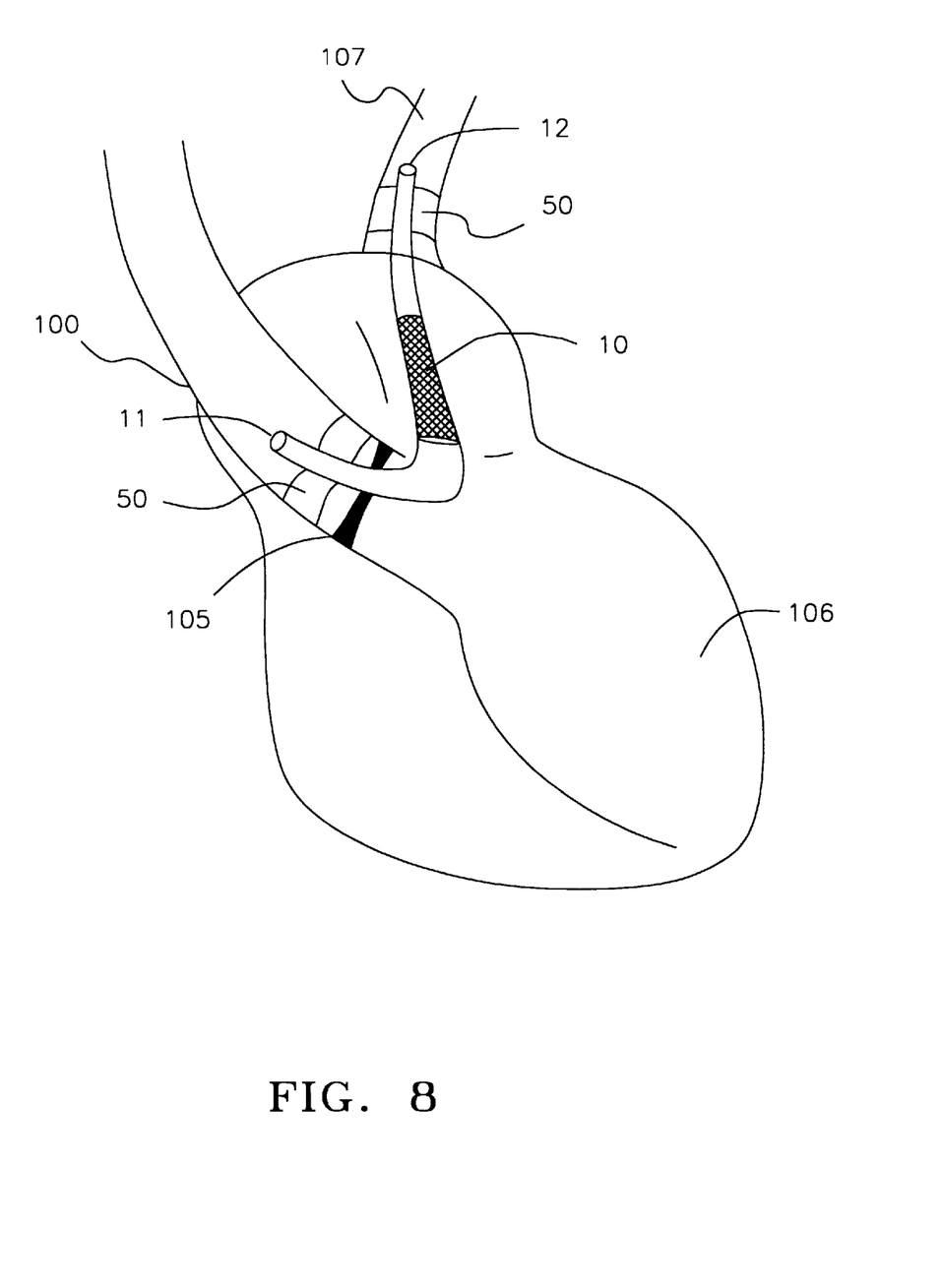
FIG. 8 depicts another embodiment of the pump having a proximal end positioned in the ascending aorta and a distal end positioned in the pulmonary vein.

The pump can also be modified to have balloon occluders mounted on proximal end 11 and distal end 12 of the pump as depicted in FIG. 8. The proximal end of the pump is positioned in ascending aorta 100. The distal end of the pump extends through aortic valves 105 into left ventricle 106 to position in pulmonary vein 107. When balloon occluders 50 are inflated, blood is prevented from entering into the left ventricular cavity, thereby allowing open left heart surgery to be performed in both beating heart or stopped heart procedures. The balloon occluder positioned in ascending aorta 100 replaces conventional aortic cross-clamping during cardiopulmonary bypass. Upon activation of pump 10, oxygenated blood is passed from pulmonary vein 107 to ascending aorta 100 to perfuse distal vital organs.

The embodiment described above can also be used in the right side of the heart to improve venous return. The proximal end of the pump is inserted in the inferior vena cava and the distal end of the pump extends into the right ventricle to position in the pulmonary artery. During stopped heart cardiac procedures, blood is delivered by the pump from the vena cava to the lungs, bypassing the right side of the heart. The pump can be inserted during surgery, either by direct stick or by the femoral route. Alternatively, the proximal end and the distal end of the pump can be inserted directly into the vena cava and the pulmonary artery, bypassing the cardiac chambers. By inflating the balloon to occlude the vena cava near the entrance to the right atrium, blood is prevented from entering the right cardiac chambers. Similarly, by inflating the balloon occlude the pulmonary artery, blood is prevented from back flowing from the lungs into the right cardiac chambers. When this embodiment is used with left-sided pumps, cardiac procedures can be performed on the stopped heart without requiring external cardiopulmonary bypass.

Figure 9:
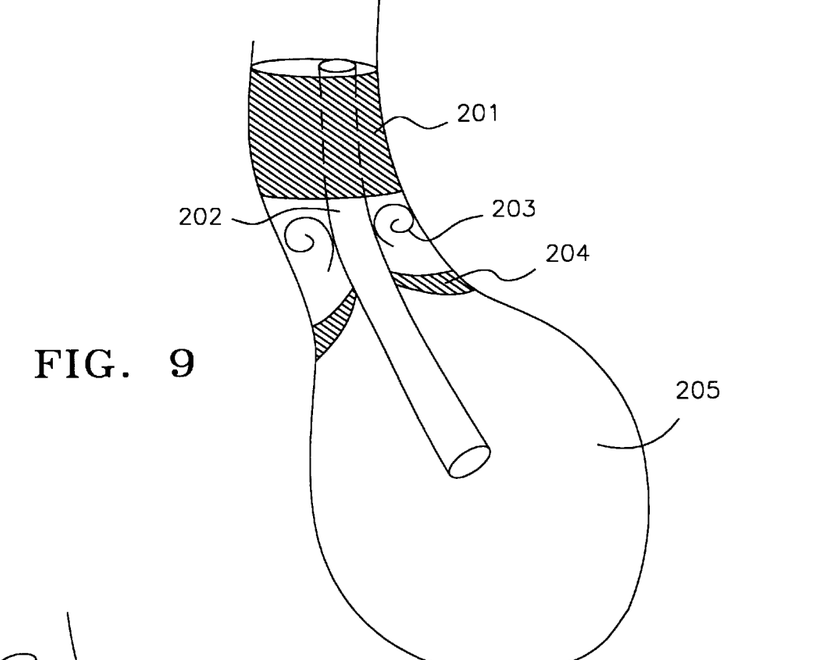
FIG. 9 depicts another embodiment of the pump/stent assembly positioned in the ascending aorta, having the pump extending into the left ventricle.
Figure 10:
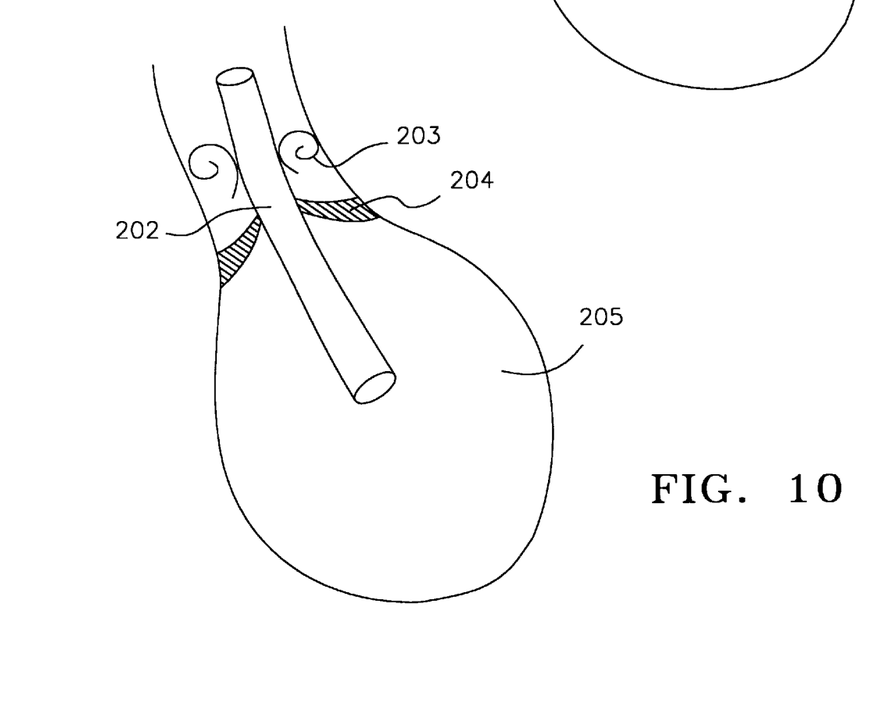
FIG. 10 depicts another embodiment of a pump/valve assembly positioned in the ascending aorta, having the pump extending into the left ventricle.
Figure 11:
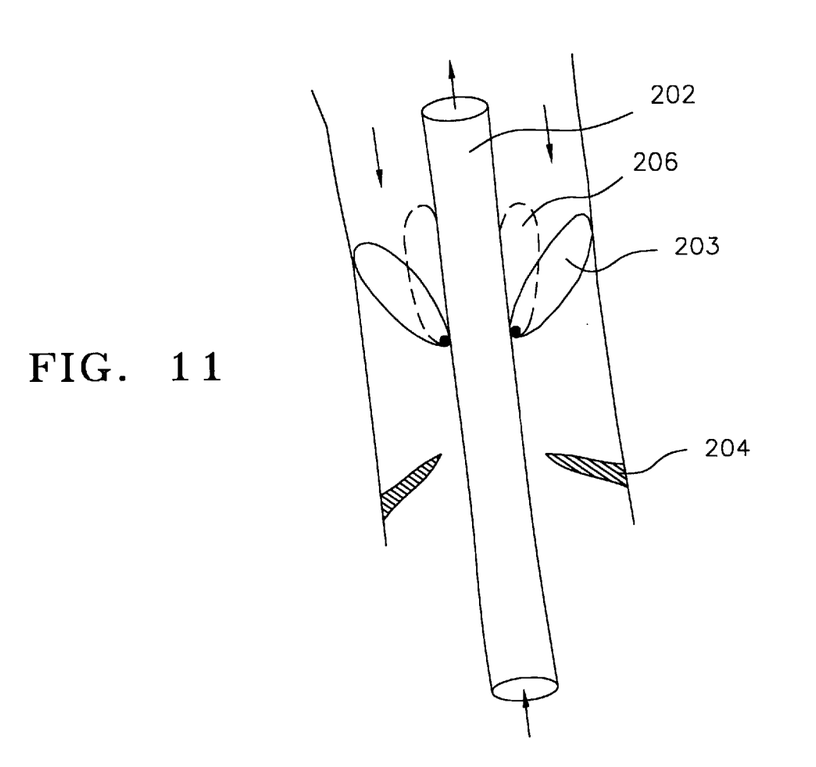
FIG. 11 depicts another embodiment of a pump/valve assembly positioned in the ascending aorta, having the pump extending into the left ventricle.

The pump can also be modified to have one or more valves mounted circumferentially about the pump as depicted in FIG. 9. This figure shows stent 201 expanded within the ascending aorta downstream of aortic valve 204. Stent 201 carries pump 202 which extends upstream through aortic valve 204 into left ventricle 205. In order to prevent back-flow of blood into the left ventricle, pump 202 may further include valve 203 mounted circumferentially about the outer diameter of pump 202. FIG. 10 depicts an alternative embodiment, wherein pump 202 engages the inner lumen of the aorta by way of valve 203 rather than a stent. FIG. 11 depicts a pump having actuatable valve system 203. The valve can be operated between a contracted state (206) and an expanded, deployed state as shown by numeral 203.

Figure 12:
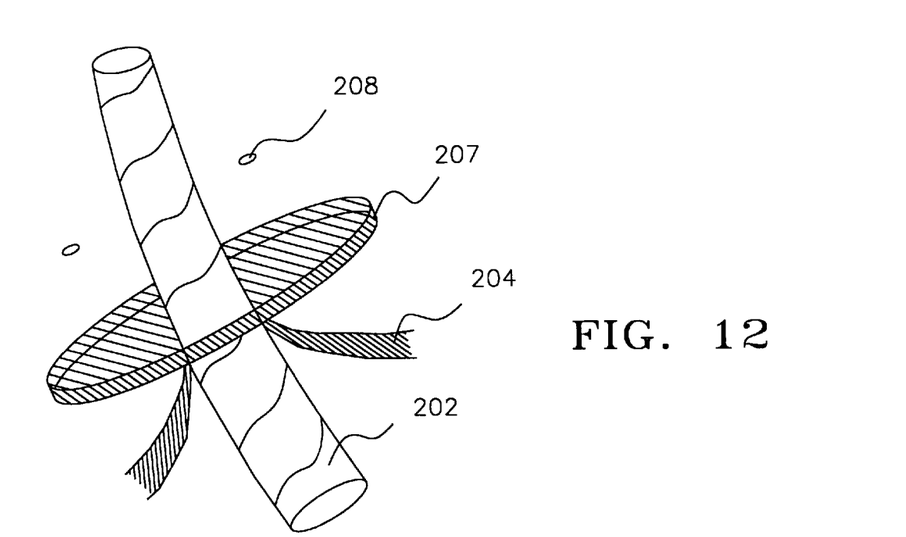
FIG. 12 depicts another embodiment of a pump mounted within an occluder plate positioned in the ascending aorta, having the pump extending into the left ventricle.

In order to avoid blockage of the coronary ostea, a pump may be implanted as depicted in FIG. 12. Instead of or in addition to a valve, pump 202 is mounted through occluder plate 207, an impermeable membrane which prevents back-flow of blood to the heart. Plate 207 is sufficiently thin so that, when expanded, plate 207 engages the lumenal diameter of the ascending aorta downstream aortic valve 204 and upstream coronary ostea 208. In this manner, the coronary ostea are not blocked, and this feature ensures perfusion of the coronary ostea.

The diameter of the pump will generally be between 0.2 and 2.0 centimeters, preferably approximately between 0.5 and 1.0 centimeters. The length of the pump will generally be between 2.0 and 15.0 centimeters, preferably approximately between 5 and 10 centimeters. The diameter of the expanded stent will be capable of expansion to an outer diameter equal to the diameter of the vessel into which it is being inserted, e.g., 3–4 cm in the aorta, 0.5–1 cm in a femoral vein or pulmonary vein. These ranges cover suitable diameters for both pediatric use and adult use and for use in vessels with various diameters. The length of the pump will generally be between 2.0 and 15.0 centimeters, preferably approximately between 5 and 10 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. Moreover, it will be apparent that all features of each embodiment as well as features disclosed in each reference incorporated herein, can be used in combination with devices illustrated in other embodiments. Accordingly, the above description should be construed as illustrative, and not in a limiting sense, the scope of the invention being defined by the following claims.

What is claimed is:

1. A method for treating cardiac insufficiency, comprising the steps of: providing a catheter having an expandable stent releasably mounted on a distal end of the catheter, the stent having a pump mounted in an interior of the stent;

inserting the distal end of the catheter into a peripheral artery;

advancing the catheter to position the stent at a region of interest within the descending aorta downstream of the left subclavian artery; expanding the stent;

releasing the stent and pump from the catheter; and activating the pump to increase arterial blood flow downstream of the pump.

2. The method of claim 1, wherein the stent is a self-expanding stent.

3. The method of claim 2, wherein the stent comprises a shape memory alloy.

4. The method of claim 3, wherein the alloy is nitinol.

5. The method of claim 1, wherein the catheter further comprises an angioplasty balloon, and wherein the stent is expanded by the step of inflating the balloon.

6. The method of claim 1, wherein the pump is a helical pump.

7. The method of claim 1, wherein the pump occupies only a fraction of an interior lumen of the stent.

8. The method of claim 1, wherein the operation of the pump is continuous.

9. The method of claim 1, wherein the pump is powered telemetrically.

10. The method of claim 1, wherein the peripheral artery is the femoral artery.

11. The method of claim 1, wherein the peripheral artery is the left subclavian artery.

12. The method of claim 1, wherein the step of expanding the stent is performed before the step of releasing the stent.

13. A method for treating cardiac insufficiency, comprising the steps of:

providing a catheter having an expandable stent releasably mounted on a distal end of the catheter, the stent having a pump mounted in an interior of the stent;

inserting the distal end of the catheter into a peripheral artery;

advancing the catheter to position the stent at a region of interest within an artery;

expanding the stent;

releasing the stent and pump from the catheter; and activating the pump to increase arterial blood flow downstream of the pump.

14. The method of claim 13, wherein the artery is a carotid artery.

15. The method of claim 14, wherein the carotid artery is the common carotid artery.

16. The method of claim 14, wherein the carotid artery is the left subclavian artery.

17. A method for treatment of varicose veins, comprising the steps of:

providing a catheter having an expandable stent releasably mounted on a distal end of the catheter, the stent having a pump mounted in an interior of the stent;

inserting the distal end of the catheter into a peripheral vein;

advancing the catheter to position the stent at a region of interest within a vein;

expanding the stent;

releasing the stent and pump from the catheter; and activating the pump to increase venous blood flow to the right atrium.

18. The method of claim 17, wherein the peripheral vein is the iliac vein.

19. The method of claim 17, wherein the peripheral vein is the femoral vein.

20. The method of claim 17, wherein the peripheral vein is the inferior vena cava.

* * * * *